US011234832B2

United States Patent
Hsieh

(10) Patent No.: US 11,234,832 B2
(45) Date of Patent: Feb. 1, 2022

(54) SUPPORT ELEMENT FOR IMPLANTATION INTO OR BETWEEN SUBJECT'S BONES, AND IMPLANT COMPONENT AND IMPLANT SYSTEM CONTAINING THE SAME

(71) Applicant: Jui-Yang Hsieh, New Taipei (TW)

(72) Inventor: Jui-Yang Hsieh, New Taipei (TW)

( * ) Notice: Subject to any disclaimer, the term of this patent is extended or adjusted under 35 U.S.C. 154(b) by 73 days.

(21) Appl. No.: 16/363,064

(22) Filed: Mar. 25, 2019

(65) Prior Publication Data

US 2020/0113709 A1  Apr. 16, 2020

(30) Foreign Application Priority Data

Oct. 15, 2018  (TW) .................................. 107213895

(51) Int. Cl.
*A61F 2/44* (2006.01)
*A61F 2/46* (2006.01)
*A61F 2/30* (2006.01)

(52) U.S. Cl.
CPC .......... *A61F 2/4465* (2013.01); *A61F 2/4611* (2013.01); *A61F 2002/30092* (2013.01); *A61F 2002/30235* (2013.01); *A61F 2002/30545* (2013.01); *A61F 2002/30593* (2013.01); *A61F 2002/30604* (2013.01)

(58) Field of Classification Search
CPC  A61F 2/4611; A61F 2/4465; A61F 2002/449; A61F 2002/4495; A61F 2/4455; A61F 2/446; A61F 2002/30092; A61F 2002/30235; A61F 2002/30545
See application file for complete search history.

(56) References Cited

U.S. PATENT DOCUMENTS

2007/0055274 A1* 3/2007 Appenzeller ...... A61B 17/8858
606/90

* cited by examiner

*Primary Examiner* — Matthew J Lawson
*Assistant Examiner* — Lisa Nguyen
(74) *Attorney, Agent, or Firm* — Muncy, Geissler, Olds & Lowe, P.C.

(57) ABSTRACT

The present invention provides a support element for implantation into or between a subject's bones, characterized in that: the support element is a hollow nestable structure having expandable elasticity, and can be in a contracted configuration or a distended configuration. The present invention also provides an implant component, comprising: the support element; and a limiting member to prevent the support element from expanding and thereby keep the support element in the contracted configuration. The present invention also provides an implant system applicable to a subject's spine, the implant system comprising: the support element as a first support element; and optionally one or a plurality of the support elements in the hollow nestable structure of the first support element. The support element can be nested until the support provided by the entire implant system reaches the desired level.

7 Claims, 17 Drawing Sheets

13

SUPPORT ELEMENT FOR IMPLANTATION INTO OR BETWEEN SUBJECT'S BONES, AND IMPLANT COMPONENT AND IMPLANT SYSTEM CONTAINING THE SAME

BACKGROUND OF THE INVENTION

1. Technical Field

The present invention relates to a device to be implanted into a subject's bone or between two connected bones. More particularly, the invention relates to an elastically expandable support element for implantation into or between a subject's bones, and an implant component and implant system containing the same.

2. Description of Related Art

The societies many of us live in are aging or aged, which raises concerns about health issues of the elderly. A senior citizen tends to suffer from osteoporosis, degenerative bone diseases, and so on due to the deterioration of body functions, or is prone to such diseases as compression fracture and degenerative disc disease that result from prolonged improper posture caused typically by insufficient muscle strength. The following paragraphs briefly state some indications for treatment in or between a subject's bones and how such treatments are performed.

Treatment within a subject's bones, or intraosseous treatment, may be indicated for bone fracture, which is common to elderly people with osteoporosis, and one notable example of which is compression fracture of the spine. While vertebral compression fractures in most patients can heal within months, the recovery period that follows is anything but easy. Persistent pain in the lower back or nerve compression may inconvenience a patient's daily life to such extent that the patient becomes bedridden, whose complications include bedsores, pneumonia, and urinary infection, among others. Some patients' vertebral compression fractures do not heal at all and hence give rise to permanent pain that may compromise the stability of the entire vertebral column, if not leading to a hunchback, in which case vertebrae adjacent to the fractured one(s) may suffer from compression fracture too, as if a domino effect occurs; this is when invasive intraosseous treatment is called for.

Treatment for vertebral compression fracture can be carried out in many ways. "Open posterior spinal fixation" and "bone fusion surgery" involve driving screws into fractured vertebrae to provide support. "Minimally invasive percutaneous vertebroplasty" is an X-ray image-guided procedure in which a bone puncture needle injects bone cement into a collapsed fractured vertebra through a tiny incision and a pedicle of the vertebra to fill the vertebra and thereby relieve pain, but this procedure cannot correct a deformed vertebra. "Minimally invasive percutaneous kyphoplasty", on the other hand, uses an inflatable balloon to restore the height of a collapsed vertebra and, after removal of the balloon, injects bone cement into the cavity formed by the inflated balloon in order to correct deformation of the collapsed vertebra to a certain degree. A relatively new method for accelerating the recovery of a vertebral compression fracture entails placing an implant into the fractured vertebra; however, an overly large implant may rupture the pedicle through which it passes during implantation, thus damaging the nearby nerves, and an implant that is not large enough for the intended collapsed vertebra can only expand the vertebra to a limited extent and therefore fails to support the vertebra adequately.

Treatment between a subject's bones, or interosseous treatment, is indicated for scoliosis, kyphosis, vertebral fracture, spondylolisthesis, spondylolysis, and degenerative disc disease for example, and nowadays typically incorporates "intervertebral fusion" with "posterior spinal fixation" to enhance the effect of rigid fixation.

Vertebrae that need intervertebral fusion can be accessed by an anterior lumbar interbody fusion (ALIF) approach, a lateral/obliquely lumbar interbody fusion (LLIF/OLIF) approach, a posterolateral lumbar interbody fusion (PLIF) approach, or a transforaminal lumbar interbody fusion (TLIF) approach. The ALIF is the golden standard in the art, allowing the largest possible support element to be implanted, but is disadvantageous in that it requires a relatively large incision, passes through the abdominal cavity, and may injure the intestinal tract, the abdominal aorta, or the ureters, if not resulting in hernia or retrograde ejaculation; technically, therefore, this approach is highly demanding on both orthopedic and neurological surgeons. The LLIF/OLIF reduces the disadvantages of the ALIF but calls for special equipment. The PLIF and the TLIF are the most widely used clinically, and yet the surgical opening tends to be obstructed and narrowed by the spinal cord and spinal nerves, making it difficult to use an adequately sized support element. Currently, intervertebral fusion can be assisted by placing an implant between the vertebrae to be fused; however, an exceedingly large implant is likely to injure the surrounding nerves, blood vessels, or other important tissues during implantation, and an implant whose size is less than required may produce overly small areas of contact with the adjacent vertebrae, causing problems attributable to undue concentration of pressure.

BRIEF SUMMARY OF THE INVENTION

With regard to implantation into a subject's bones, the conventional open posterior spinal fixation procedure and bone fusion procedure have the following drawback. In cases where screws may easily get loose because of a patient's osteoporotic conditions, there is no other choice than to enlarge the incision and use more screws to fixate more vertebrae, but more complications may also ensue from such a time-consuming, blood-losing spinal fixation operation. Some common complications an elderly patient may develop are stiffness in the back, cardiopulmonary failure, and infection. As to minimally invasive percutaneous vertebroplasty or kyphoplasty, the "bone cement" used in the operation may leak. A serious leak of bone cement into blood vessels may result in arterial thrombosis, venous thrombosis, or stroke. If a lot of bone cement leaks to the spinal cord or nerve roots and subsequently cures (generating high heat during the curing process), the surrounding nerves may be severely compressed or damaged. Moreover, when bone cement exists permanently as a filler in a vertebra, the low bone-compatibility and extremely high hardness of bone cement may give rise to bone resorption, hinder the healing of a fracture in the vertebra, or even fracture a neighboring vertebra.

As for implantation between a subject's bones, the conventional devices for intervertebral fusion are the intervertebral cages, which can be roughly divided into those of a unitary structure and those of a composite structure. Common unitary-structure cages are in the shape of a disc-shaped, straight bullet-shaped, or banana-shaped for example, with a simple structural design that depends on a complicated tool for implantation and for preventing nerve and blood vessel injuries. Clinically, therefore, a unitary-structure intervertebral cage often falls short of its required dimensions such that the areas of contact between the cage and the adjacent vertebrae are not large enough to avoid pressure concentration (which may cause a subsidence or a extrusion of the intervertebral cage from the vertebrae) or promote intervertebral fusion (the failure of which may lead to the formation of a pseudoarthrosis). Composite-structure intervertebral cages either incorporate a screw or have an expandable structure. The screw-type cages, though featuring enhanced fixation, add to the difficulty of surgical operation and are applicable only in anterior intervertebral fusion. The expandable-structure intervertebral cages can be further divided into the medial-lateral expansion type and the caudal-cranial expansion type, both of which enable relatively large areas of contact and increased fixation but have rather intricate mechanical structures, including, for example, a large number of articulations and points of stress concentration. These complex structures not only limit the amount of bone graft packaged that can be put into each cage, but also increase the chances of long-term fatigue failure and pseudoarthrosis formation between vertebrae.

As is well known in the art, implants in or between a subject's bones must not be complicated mechanical assemblies, or they tend to fatigue, disintegrate, or fail after persistent use in the human body. In addition, such implants are preferably highly biocompatible or even conducive to the healing of bone fractures and therefore must not include materials that are rarely used, or not allowed to be used, in the human body. All the foregoing issues regarding bone implants remain to be addressed by medical experts and scientific researchers.

In view of the deficiencies and shortcomings of conventional techniques in the treatment of bone indications, the primary objective of the present invention is to provide a support element for implantation into or between a subject's bones, characterized in that: the support element is a hollow nestable structure having expandable elasticity, and is in a contracted configuration before implantation into a bone or between bones, and expands into a distended configuration after implantation into or between the bones.

Further, the bone is a vertebra.

Further, the support element is a reticular structure.

Further, the material of the support element comprises metal or elastomer.

Further, the material of the support element comprises nickel-titanium alloys.

Further, the support element is a hollow cylinder.

Another objective of the present invention is to provide an implant component for implantation into or between a subject's bones, comprising: the aforesaid support element; and a limiting member, provided around the support element to prevent the support element from expanding and thereby keep the support element in the contracted configuration.

Further, the implant component further comprises a guiding member which is configured to pass through the center of the hollow nestable structure of the support element.

Another objective of the present invention is to provide an implant system applicable to a subject's spine, wherein the spine comprises a vertebra with a pedicle, the implant system comprising: the aforesaid support element as a first support element; and optionally one or a plurality of the aforesaid support elements in the hollow nestable structure of the first support element in the distended configuration, wherein the one or the plurality of support elements are nested sequentially in the distended configuration within the hollow nestable structure of the first support element in the distended configuration.

Another objective of the present invention is to provide an implant system applicable to a subject's spine, wherein the spine comprises an intervertebral, the implant system comprising: the aforesaid support element as a first support element; and optionally one or a plurality of the aforesaid support elements in the hollow nestable structure of the first support element in the distended configuration, wherein the one or the plurality of support elements are nested sequentially in the distended configuration within the hollow nestable structure of the first support element in the distended configuration.

Therefore, the support element, the implant component, and the implant system of the present invention have the following beneficial effects:

1. The present invention provides a support element that stays in a contracted configuration, and hence remains relatively small, before implantation into a subject's bone or between two connected bones so as to facilitate the implantation, allowing a minimally invasive, small-incision surgical operation to be performed clinically.

2. Once implanted into the subject's bone or between the connected bones, the support element of the present invention expands elastically into a distended configuration and contacts to the inner wall of the bone to be treated or the corresponding outer walls of the bones to be treated, thereby expanding the fractured/collapsed bone or providing support between the connected bones. This support element is an improvement over the one-size implants used in the conventional implantation techniques because an existing one-size implant cannot "be a single micro-unit before implantation into or between a subject's bones and turn into a larger yet complete block after the implantation". In addition, unlike the traditional one-size implants, the support element of the invention will not rupture the affected bone structure (e.g., a pedicle) or injure the surrounding nerves (e.g., the spinal cord or spinal nerves), blood vessels (e.g., the abdominal aorta or the vertebral arteries), or other important tissues (e.g., the ureters) during implantation; nor provide inadequate support due to an expediently less-than-required size.

3. If necessary, a plurality of the support elements of the present invention can be nested inside one another in the distended configuration after implantation into a bone or between two connected bones, and the nesting process can continue until the support provided by the entire implant system reaches the desired level. Thus, in the limited, tiny space in a single collapsed bone or between two connected bones, a plurality of the support elements of the invention can be put together to effectively restore the single collapsed bone or provide support between the connected bones. The number of the support elements to be implanted depends on the height of the bone to be restored or the distance between the connected bones to be supported. Theoretically, a single bone or the space between two connected bones can be filled with as many support elements of the invention as needed.

4. When a plurality of the support elements of the present invention are implanted, all the support elements expand elastically in the same direction, and each support element contacts tightly to either the inner wall of a bone, the corresponding outer walls of adjacent bones, or the inner wall of a previous support element and hence will not come loose.

5. The support element of the present invention has a hollow nestable structure, which can be filled with an autologous, heterologous, or artificial bone graft as clinically needed to help increase the density of, grow, and thereby heal a fractured bone.

DETAILED DESCRIPTION OF THE INVENTION

The details and technical solution of the present invention are hereunder described with reference to accompanying drawings. For illustrative sake, the accompanying drawings are not drawn to scale. The accompanying drawings and the scale thereof are not restrictive of the present invention.

The use of "or" means "and/or" unless stated otherwise. The use of "comprise" means not excluding the presence or addition of one or more other components, steps, operations, or elements to the described components, steps, operations, or elements, respectively. Similarly, "comprise," "comprises," "comprising" "include," "includes," and "including" are interchangeable and not intended to be limiting. As used herein and in the appended claims, the singular forms "a," "an," and "the" include plural referents unless the context dictates otherwise. The terms "a", "an," "the," "one or more," and "at least one," for example, can be used interchangeably herein.

The present invention is more detailed illustrated by the example embodiments as below. While example embodiments are disclosed herein, it should be understood that they are used for illustrating the present invention, not for limiting the scope of the present invention.

The present invention provides a support element, an implant component, and an implant system that are configured not only for implantation into or between human bones, but also for use in other vertebrates such as amphibians, reptiles, birds, and mammals. Furthermore, the support element, implant component, and implant system of the invention can be used in or between any suitable bones, preferably vertebrae.

Figure 1:
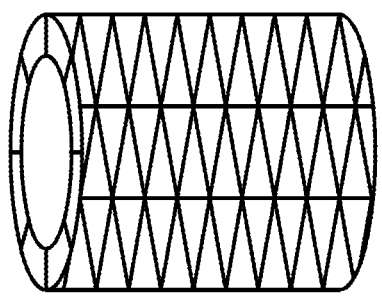
FIG. 1 is a schematic structural diagram showing the support element according to a preferred embodiment of the present invention in a contracted configuration.
Figure 2:
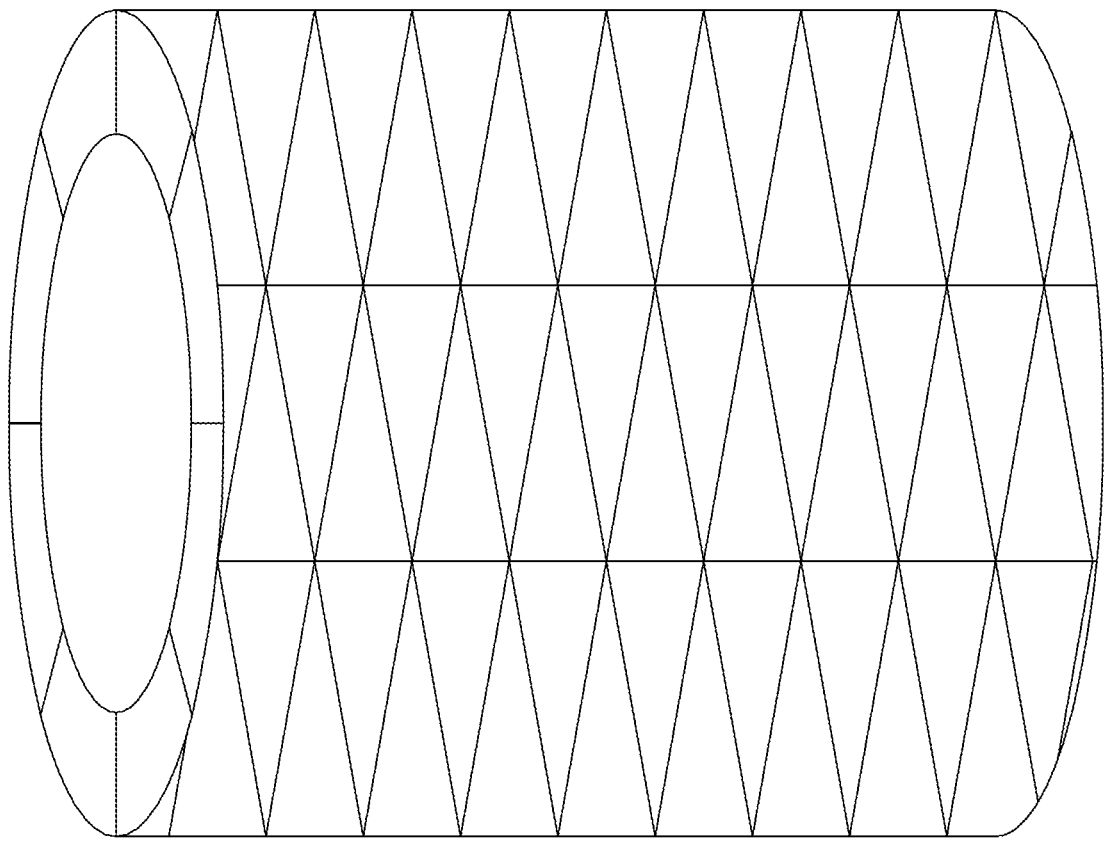
FIG. 2 is a schematic structural diagram showing the support element in FIG. 1 in a distended configuration.

Please refer to FIG. 1 and FIG. 2 for schematic structural diagrams of the support element for implantation into or between a subject's bones according to a preferred embodiment of the present invention. The support element is shown in FIG. 1 as in a contracted (i.e., non-expanded) configuration and in FIG. 2 as in a distended (i.e., expanded) configuration.

As shown in FIG. 1 and FIG. 2, the support element for implantation into or between a subject's bones is characterized in that it is a hollow nestable structure, having expandable elasticity, and is in a contracted configuration (see FIG. 1) before implantation into a bone or between two connected bones, and expands into a distended configuration (see FIG. 2) after implantation into the bone or between the connected bones.

Preferably, both the contracted support element 11 and the distended support element 12 have a hollow structure. More specifically, each of the contracted support element 11 and the distended support element 12 at least has a hollow structure through which a needle can pass. It is even more preferable that the empty space in the hollow structure of the contracted support element 11 can expand from a space that allows the passage of a needle into a substance receiving space of the distended support element 12 due to the inherent elastic expansion property of the support element, wherein the substance to be received may be, for example, an autologous bone graft, a heterologous bone graft, an artificial bone graft, or another support element or a plurality of other support elements of the same structural design as the contracted support element 11 and the distended support element 12; the present invention has no limitation on such substances. In a preferred embodiment, the contracted support element 11 and the distended support element 12 of the invention may be hollow cuboids, hollow spheres, hollow cylinders, or other regular or irregular three-dimensional structures with a cavity, wherein the contracted support element 11 and the distended support element 12 may have the same shape or have different shapes respectively. In a more preferred embodiment, both the contracted support element 11 and the distended support element 12 of the invention are hollow cylinders. In another preferred embodiment, the support element of the invention is a reticular structure, which is advantageous in that it not only produces a supporting effect similar to that of trabeculae, but also facilitates fusion between the support element itself or the filler therein and the surrounding ossein, thereby assisting in the healing of a bone fracture. Besides, the size of the support element of the invention (including the contracted support element 11 and the distended support element 12) is preferably based on the dimensions of the target space in which the support element is to be implanted. For example, if implantation is to take place where an intervertebral disc lies, the support element may have a slender design to adapt to the flat disc-shaped intervertebral space. That is to say, the support element of the invention can be adjusted and varied as needed, without limitation on size.

In a preferred embodiment, the material of the support element of the present invention includes a biocompatible material such as metal and/or elastomer. Suitable metals include but are not limited to magnesium alloys, tantalum alloys (e.g. TaC or TaN), titanium alloys (e.g. Gummetal®), nickel-titanium alloys, nickel-titanium-copper alloys, cobalt-chromium alloys (e.g. Elgiloy®), cobalt-chromium-nickel alloys (e.g. Phynox®), chromium-tungsten-nickel alloys (e.g. L605), cobalt-chromium-vanadium alloys, cobalt-nickel-chromium-molybdenum alloys (e.g. MP35N or MP20N), stainless steel (e.g. 316, 316L, or 304), and metallic glass. Suitable elastomers include polymers, copolymers, composite materials, and mixtures of the above, such as but not limited to styrene-based elastomers, olefin-based elastomers, polyolefin-based elastomers, polyurethane-based thermoplastic elastomers, polyamides, polybutadienes, polyisobutylene, poly(styrene-butadiene-styrene), poly(2-chloro-1,3-butadiene), silicones, thermoplastic polyurethanes (TPU), polyurethanes (PU), polysiloxanes (e.g. PDMS or h-PDMS), poly(methyl methacrylate) (PMMA), polyetheretherketone (PEEK), ultra-high-molecular-weight polyethylenes (UHMWPE), and silicon rubber. In a more preferred embodiment, the material of the support element of the invention includes a nickel-titanium alloy, such as a nickel-titanium shape-memory alloy (e.g. Nitinol or Nitinol-DFT®-Pt). This embodiment is advantageous in that the superior elasticity and shape memory of nickel-titanium alloys make it possible to preset the dimensions of the intended distended support element 12, to manufacture the distended support element 12 accordingly, and to compress or fold the distended support element 12 into the smaller contracted support element 11 so that, once the limiting member is removed (e.g., after implantation into a bone or between bones), the contracted support element 11 expands automatically and elastically to the preset dimensions to achieve the objective of "being a single micro-unit before implantation into or between a subject's bones and expanding into a larger yet complete block after the implantation". Furthermore, nickel-titanium alloys have such mechanical properties as being highly resistant to pressure, tension, and torsion; are corrosion-resistant, highly biocompatible, and shock-absorbent; and are therefore suitable for implantation into or between bones.

Figure 3:
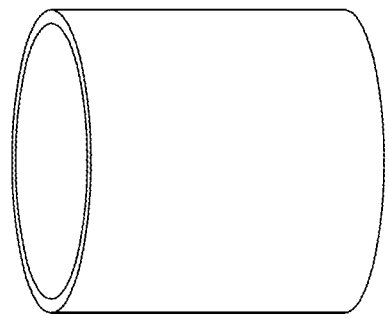
FIG. 3 is a schematic structural diagram of the limiting member of the implant component according to a preferred embodiment of the invention.
Figure 4:
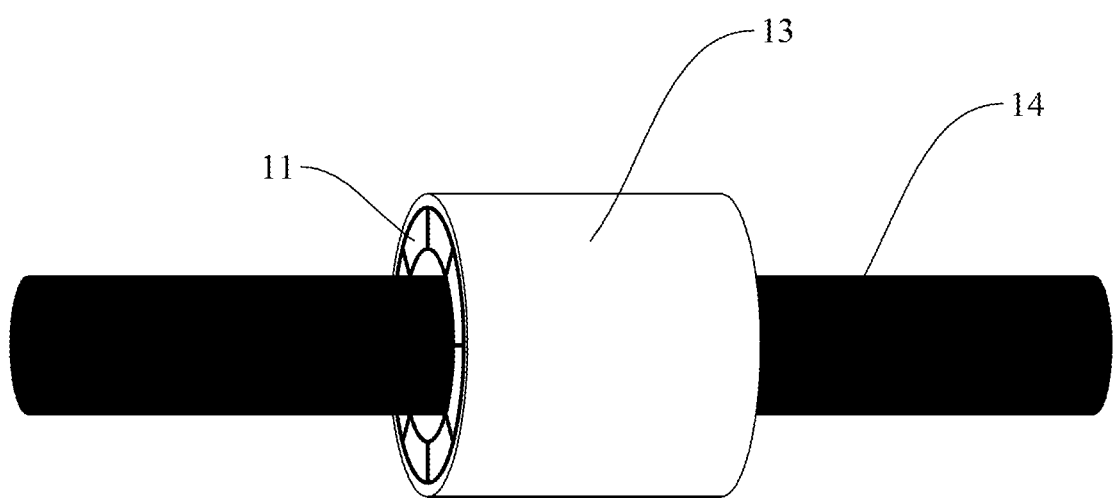
FIG. 4 is a schematic assembled view of the implant component whose limiting member is shown in FIG. 3.
Figure 5:
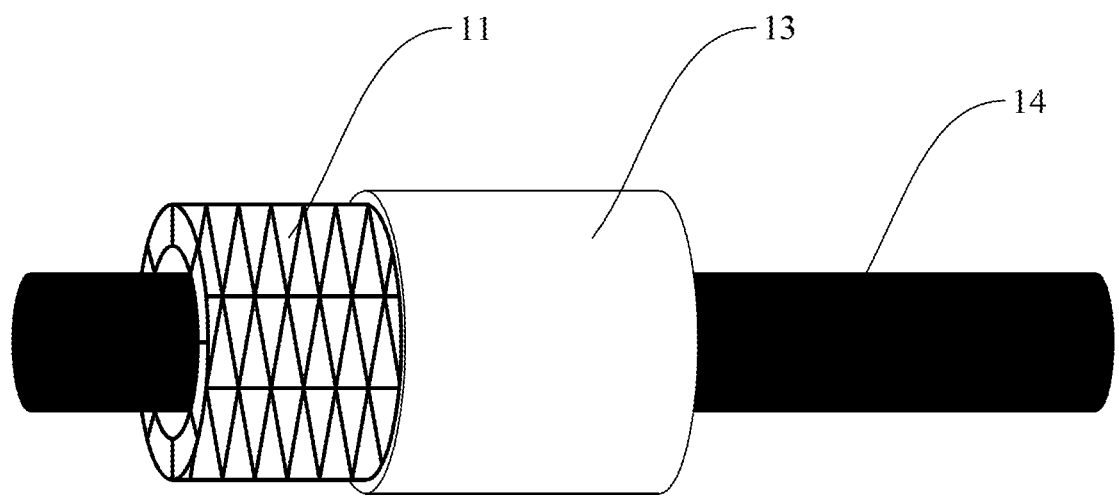
FIG. 5 is another schematic assembled view of the implant component in FIG. 4.

Please refer to FIG. 3 to FIG. 5 respectively for a schematic structural diagram of the limiting member 13 of the implant component 10 for implantation into or between a subject's bones according to a preferred embodiment of the present invention, a schematic assembled view of the implant component 10, and a schematic assembled view showing removal of the limiting member 13.

As shown in FIG. 3 to FIG. 5, the implant component 10 for implantation into or between a subject's bones includes the foregoing support element, the limiting member 13 (see FIG. 3), and preferably also a guiding member 14 (see FIG. 4 and FIG. 5) configured to pass through the center of the hollow nestable structure of the support element. The limiting member 13 and the guiding member 14 are auxiliary elements designed to facilitate implantation of the support element into or between a subject's bones and will be removed from the subject's body when implantation of the support element is completed.

The limiting member 13 is provided around the support element to prevent the support element from expanding and thereby keep the support element in the contracted configuration. In other words, the constraint imposed on the support element by the limiting member 13 can be removed (see FIG. 5) at a proper time (e.g., after implantation into a bone or between bones), allowing the support element to expand automatically and elastically to its preset dimensions. In a preferred embodiment, the material of the limiting member 13 of the present invention may include metal, plastic, rubber, glass fibers, ceramic, or a combination of the above. In a preferred embodiment, the limiting member 13 of the invention is shaped to receive the hollow cylindrical body of the contracted support element 11.

The guiding member 14 is an auxiliary element configured to guide the support element to the implantation site and is preferably rigid. In a preferred embodiment, the material of the guiding member 14 of the present invention may include metal.

Please refer to FIG. 6 to FIG. 12 for a human spine S (FIG. 6), the structure of the first lumbar vertebra L1 (FIG. 7), and how the implant systems 100, 200 according to two preferred embodiments of the present invention implant one or a plurality of support elements into a subject's bone (FIG. 8 through FIG. 12).

Figure 6:
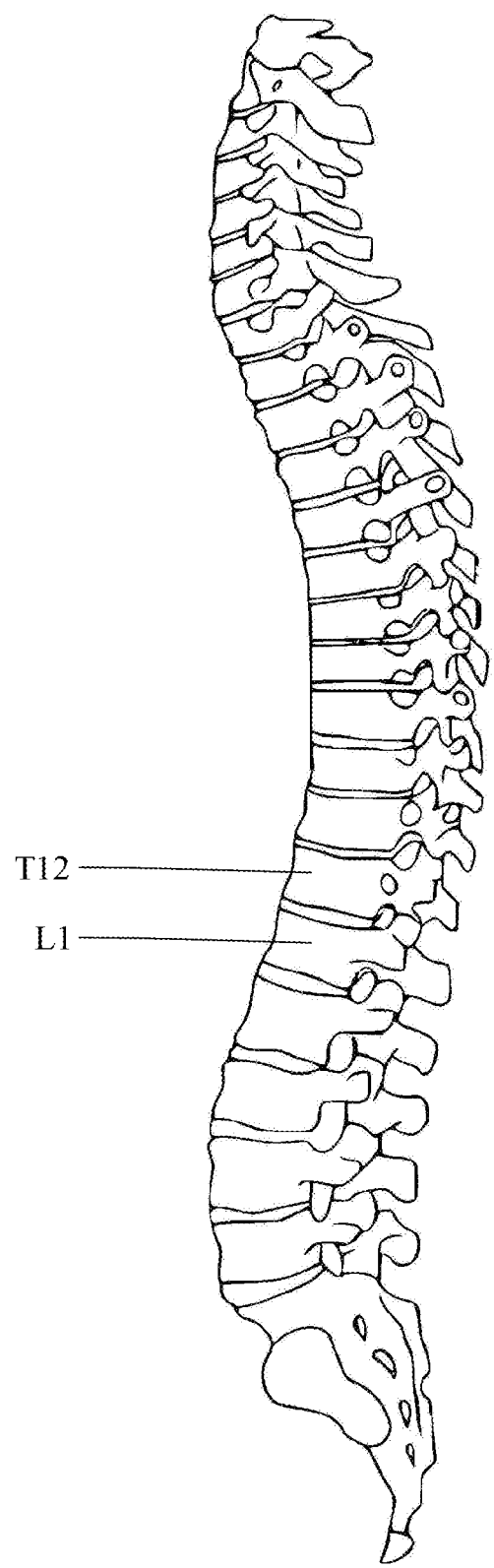
FIG. 6 is a left side view of a human spine.
Figure 7:
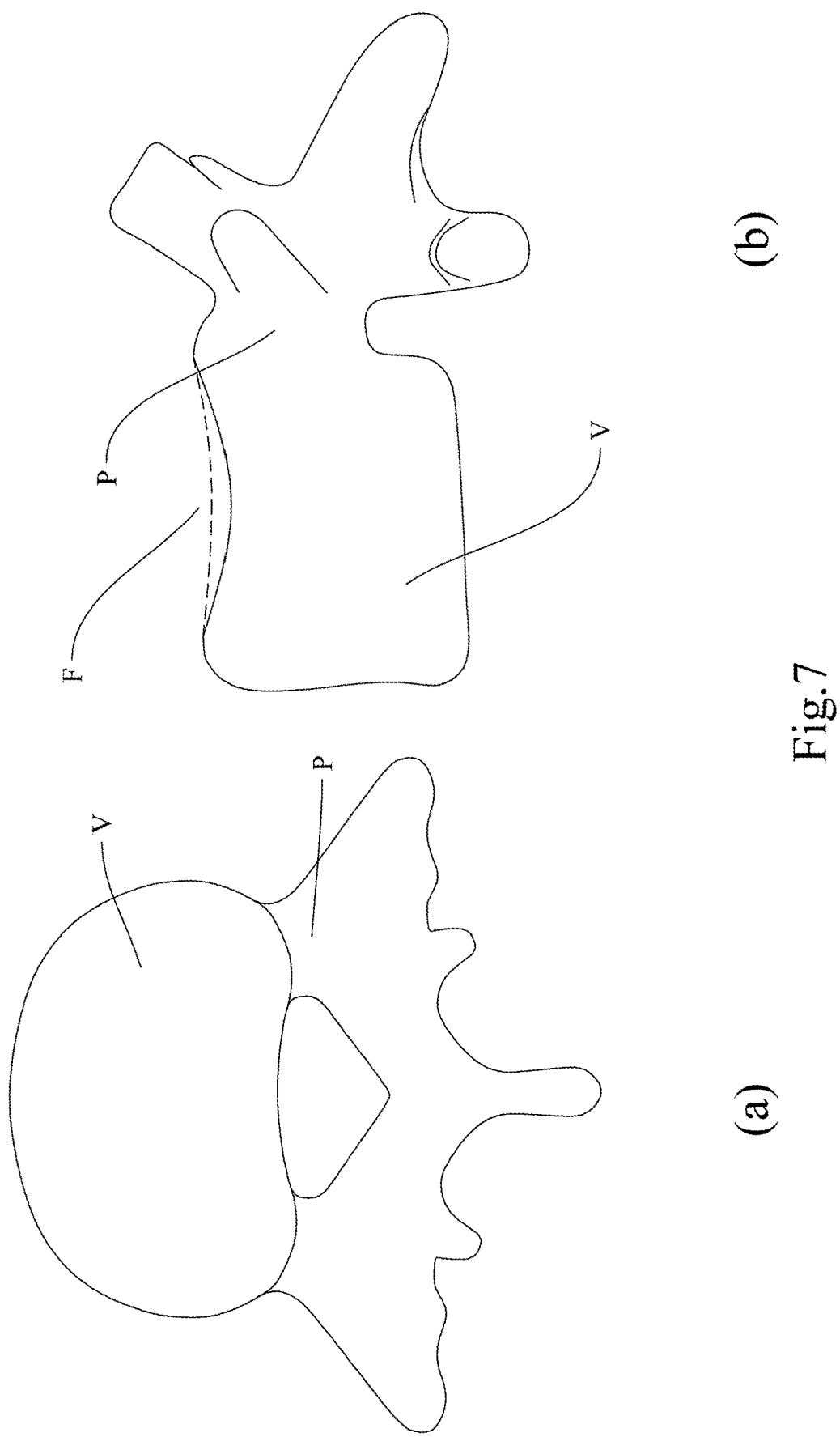
FIG. 7 includes an axial view (a) and a left side view (b) of the first human lumbar vertebra, which is collapsed due to compression fracture.

The implant systems 100, 200 are configured for implantation into a subject's bones and are preferably applied to a subject's vertebral column, or spine S, which includes a vertebra V with a pedicle P. As shown in FIG. 6, a complete human spine includes a plurality of vertebrae, and the first lumbar vertebra L1 is referred to herein by way of example. The first lumbar vertebra L1 shown in FIG. 7 has a collapsed endplate resulting from a compression fracture F, which is one of the various forms of vertebral compression fracture. The implant systems 100, 200 of the present invention can be used to implant the foregoing implant component 10 into the first lumbar vertebra L1 with the compression fracture F in the following manner.

Figure 8:
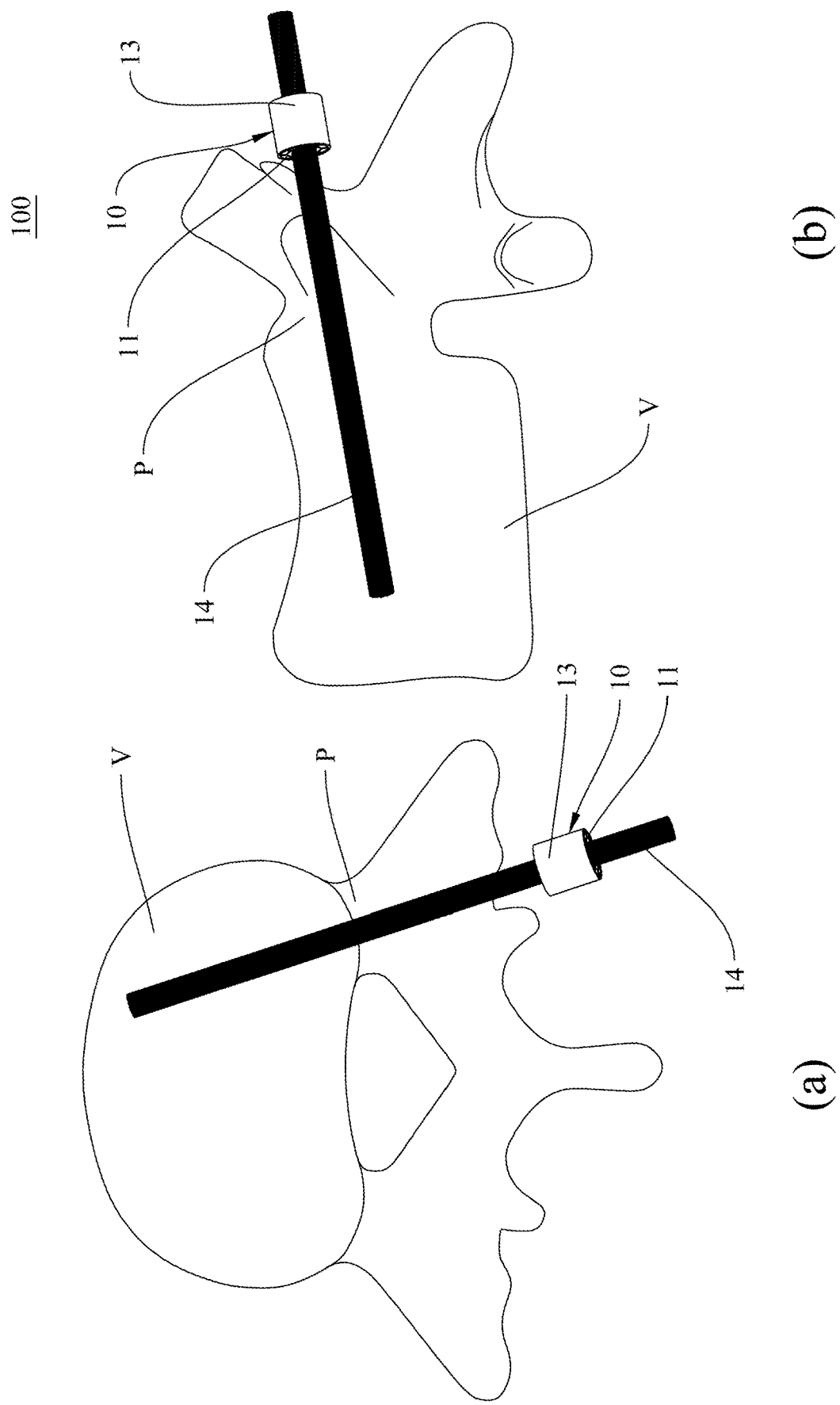
FIG. 8 includes an axial view (a) and a left side view (b) showing how the implant system according to a preferred embodiment of the invention is operated (to guide the insertion of a support element in a contracted configuration)

To begin with, referring to FIG. 8, the guiding member 14 is driven into the collapsed vertebra V (i.e., the first lumbar vertebra L1) through the pedicle P of the first lumbar vertebra L1. To position the guiding member 14 in the vertebra V properly, a hollow bone puncture needle (not shown) bores a hole through the pedicle P with the guidance of X-ray images and thus enters the collapsed vertebra V, a steel guide needle (not shown) is placed into the vertebra V through the channel in the bone puncture needle, and then the bone puncture needle is removed, before the guiding member 14 is inserted into the vertebra V along the steel guide needle.

Figure 9:
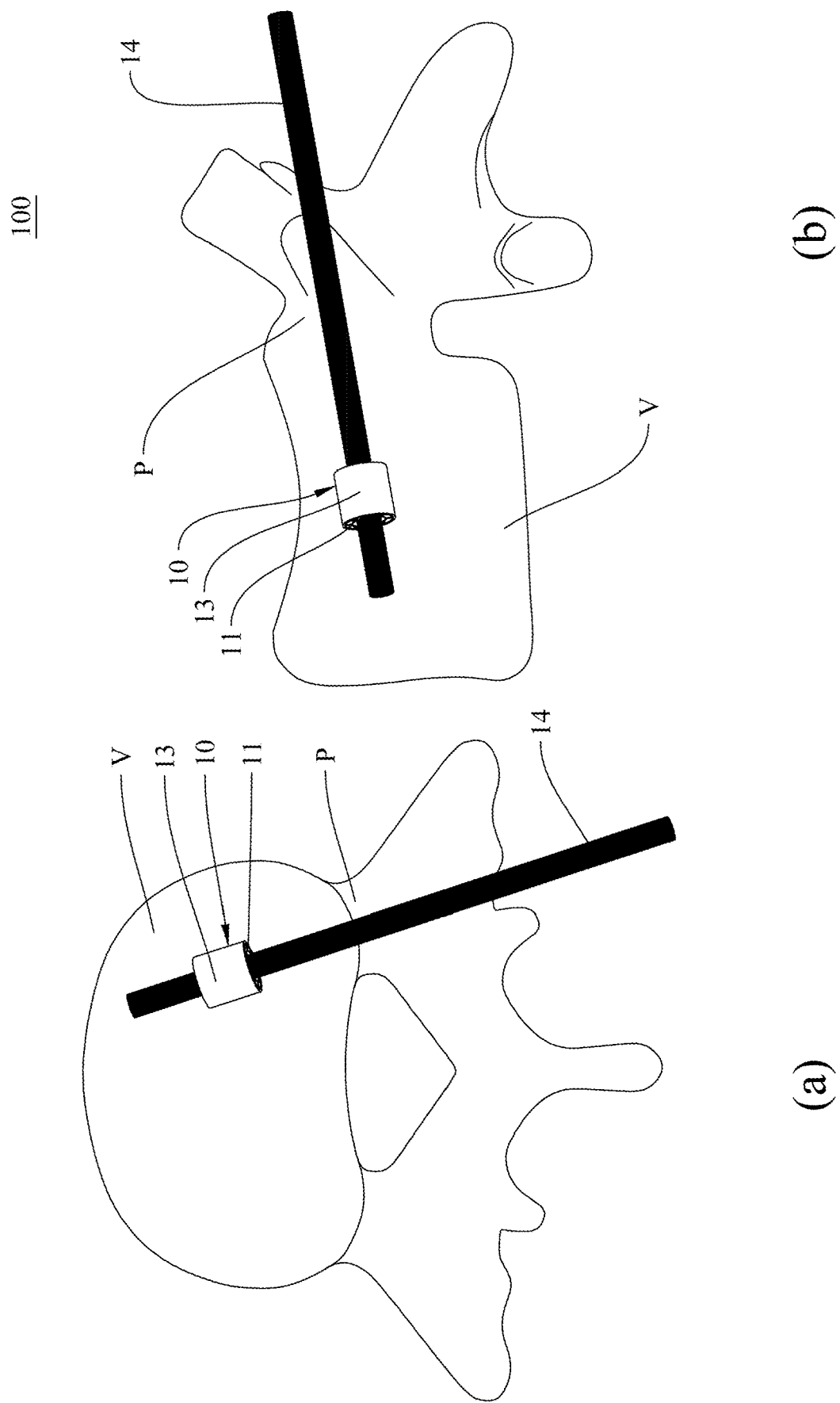
FIG. 9 includes an axial view (a) and a left side view (b) showing how the implant system in FIG. 8 is further operated (to position the support element)

Once the guiding member 14 is in place, referring to FIG. 9, the contracted (i.e., non-expanded) support element 11, which is constrained within the limiting member 13, is guided into the vertebra V along the guiding member 14 until the target position is reached, e.g., until the contracted support element 11 is properly positioned at the fracture F.

Figure 10:
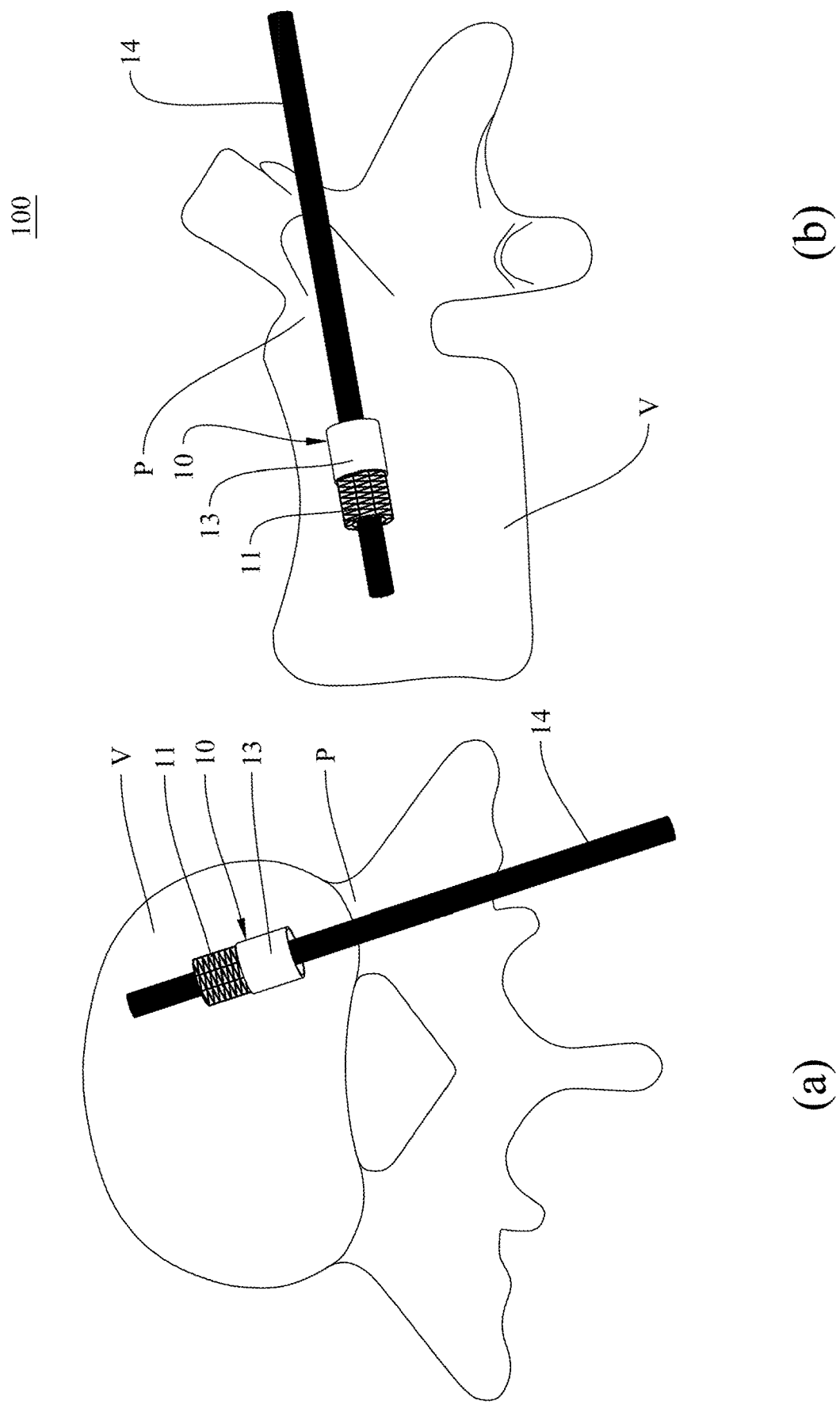
FIG. 10 includes an axial view (a) and a left side view (b) showing how the implant system in FIG. 9 is further operated (to remove the limiting member)

Next, referring to FIG. 10, the limiting member 13 is removed from the contracted support element 11.

Figure 11:
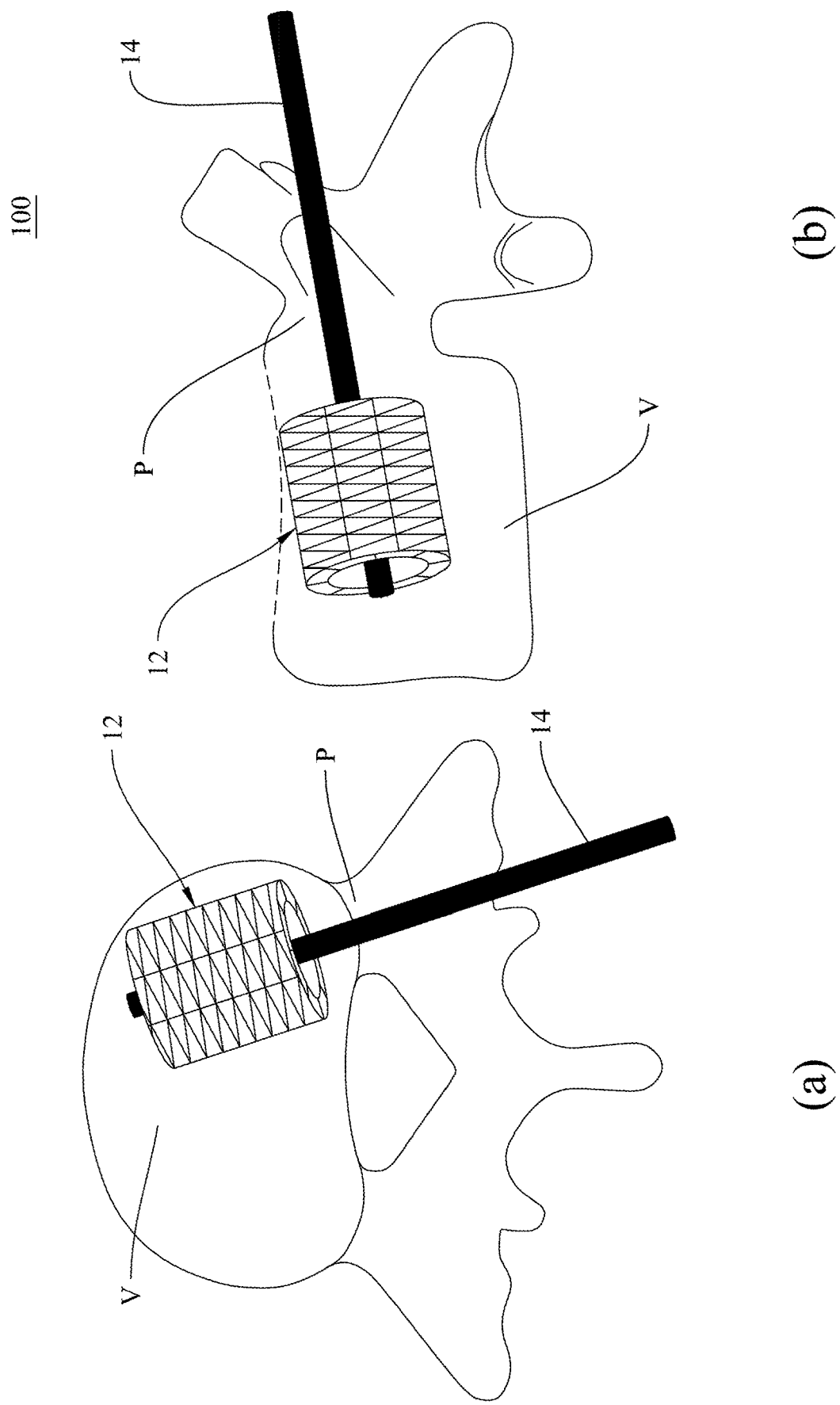
FIG. 11 includes an axial view (a) and a left side view (b) showing how the implant system in FIG. 10 is further operated (allowing the support element to expand into a distended configuration)

Finally, referring to FIG. 11, the contracted support element 11 expands elastically to the preset dimensions (i.e., turns into the distended support element 12) thanks to its shape memory and tightly contacts to the inner wall of the vertebra V. The distended support element 12 provides support in the collapsed vertebra V and thereby restores the vertebra V partially. If necessary, a plurality of support elements can be implanted horizontally or vertically (not shown) to enlarge the supported area. Thus, the support element of the present invention and the implant systems 100, 200 containing the same overcome the prior art drawback that a one-size implant placed into a vertebra V may injure the nerves around the affected pedicle or provide inadequate support due to a mismatch in size.

Figure 12:
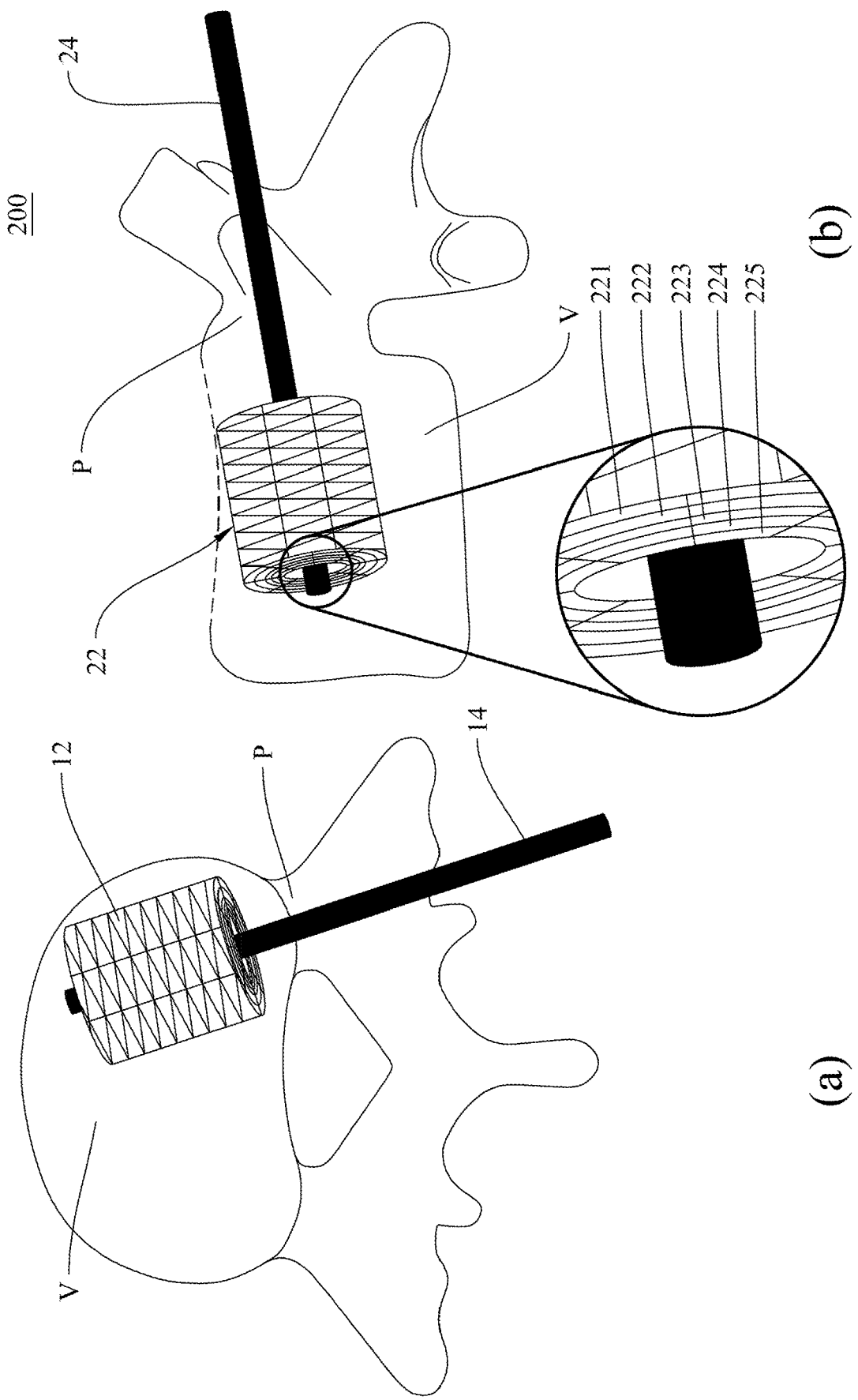
FIG. 12 includes an axial view (a) and a left side view (b) showing how the implant system according to another preferred embodiment of the invention is operated (to have a plurality of support elements nested in one another)

The implant system 200 includes the foregoing support element as the first support element 221 and another foregoing support element (or a plurality of other foregoing support elements) in the distended hollow nestable structure of the first support element 221. The one or the plurality of other support elements are nested sequentially, in the distended configuration, in the hollow nestable structure of the first support element 221 as shown in FIG. 12. To nest a plurality of support elements 22 within one another, a support element is implanted into the vertebra V with the guidance of the guiding member 24 in the same way as described above and then expands into the distended configuration to serve as the first support element 221, which tightly contacts to the inner wall of the vertebra V, and a second support element 222, which is slightly smaller than the first support element 221, is implanted at the same site by the same method and, after elastic expansion, tightly contacts to the inner wall of the first support element 221 to further restore, and provide more support for, the collapsed vertebra V. If necessary, an appropriate number of support elements can be further implanted into the collapsed vertebra V. For example, a third support element 223, a fourth support element 224, and a fifth support element 225 are sequentially guided into and nested in the vertebra V to form the nested configuration shown in FIG. 12 and thereby achieve the desired supported height for full restoration.

FIG. 13 to FIG. 17 show how the implant systems 300, 400 according to another two preferred embodiments of the present invention implant one or a plurality of support elements between a subject's bones.

The implant systems 300, 400 are configured for interosseous implantation and are preferably applied to a subject's spine S, which includes an intervertebral disc D. The support elements used in the implant systems 300, 400 may have a slender shape to suit the space where the intervertebral disc D is. Here, the intervertebral disc D between the twelfth thoracic vertebra T12 and the first lumbar vertebra L1 in FIG. 6 is referred to by way of example. The implant systems 300, 400 can be used to implant an implant component 30 into the interosseous space (i.e., the intervertebral disc D) between the twelfth thoracic vertebra T12 and the first lumbar vertebra L1 as detailed below.

It should be pointed out first that a support element for implantation between two connected bones is preferably longer and thinner than one for implantation into a bone.

Figure 13:
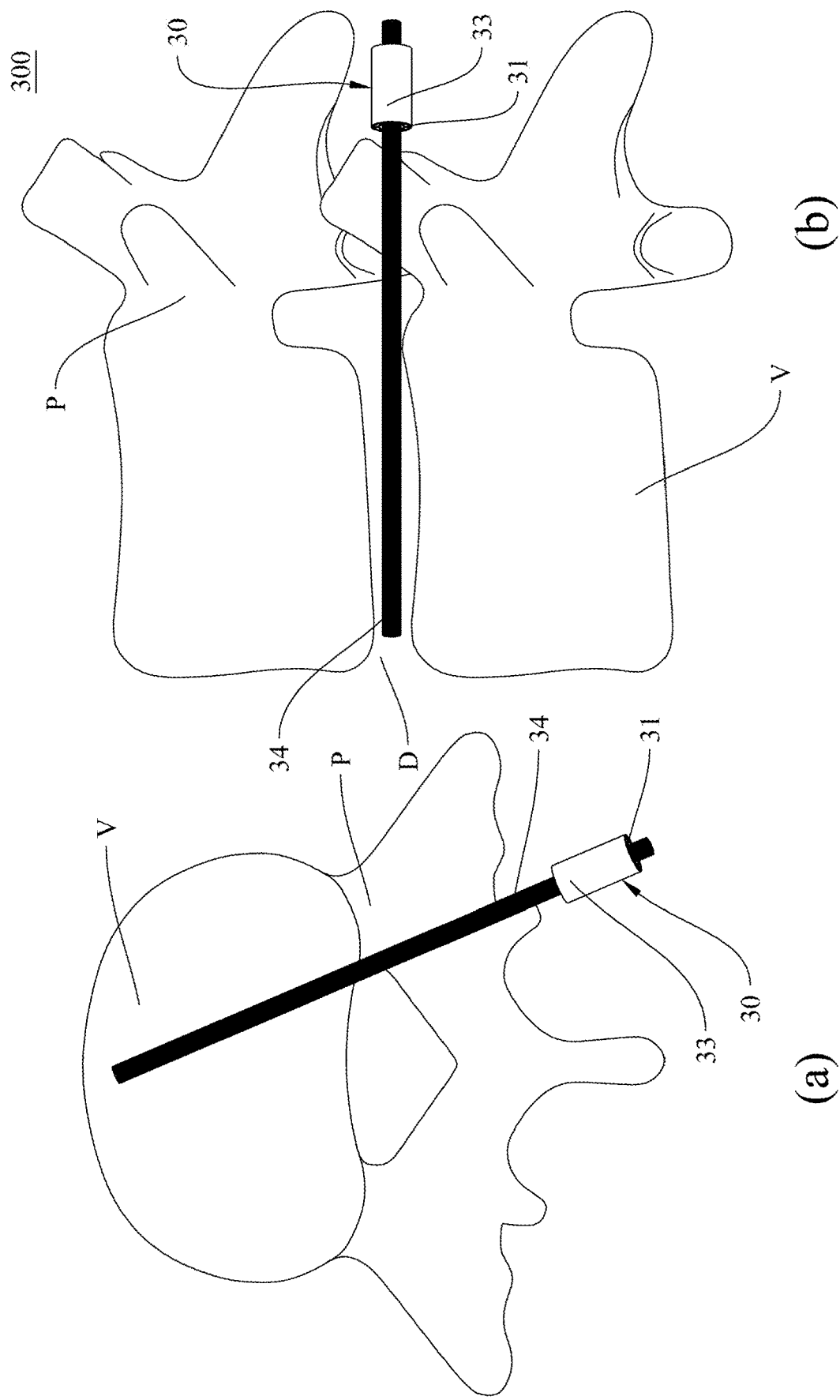
FIG. 13 includes an axial view (a) and a left side view (b) showing how the implant system according to yet another preferred embodiment of the invention is operated (to guide the insertion of a support element in a contracted configuration)

Referring to FIG. 13, the implantation process begins by inserting the guiding member 34 through the intervertebral disc D into the interosseous space. To position the guiding member 34 in the intervertebral disc D properly, a hollow bone puncture needle (not shown) is driven into the intervertebral disc D with the guidance of X-ray images, a steel guide needle (not shown) is placed into the intervertebral disc D through the channel in the bone puncture needle, and then the bone puncture needle is removed, before the guiding member 34 is inserted into the intervertebral disc D along the steel guide needle.

Figure 14:
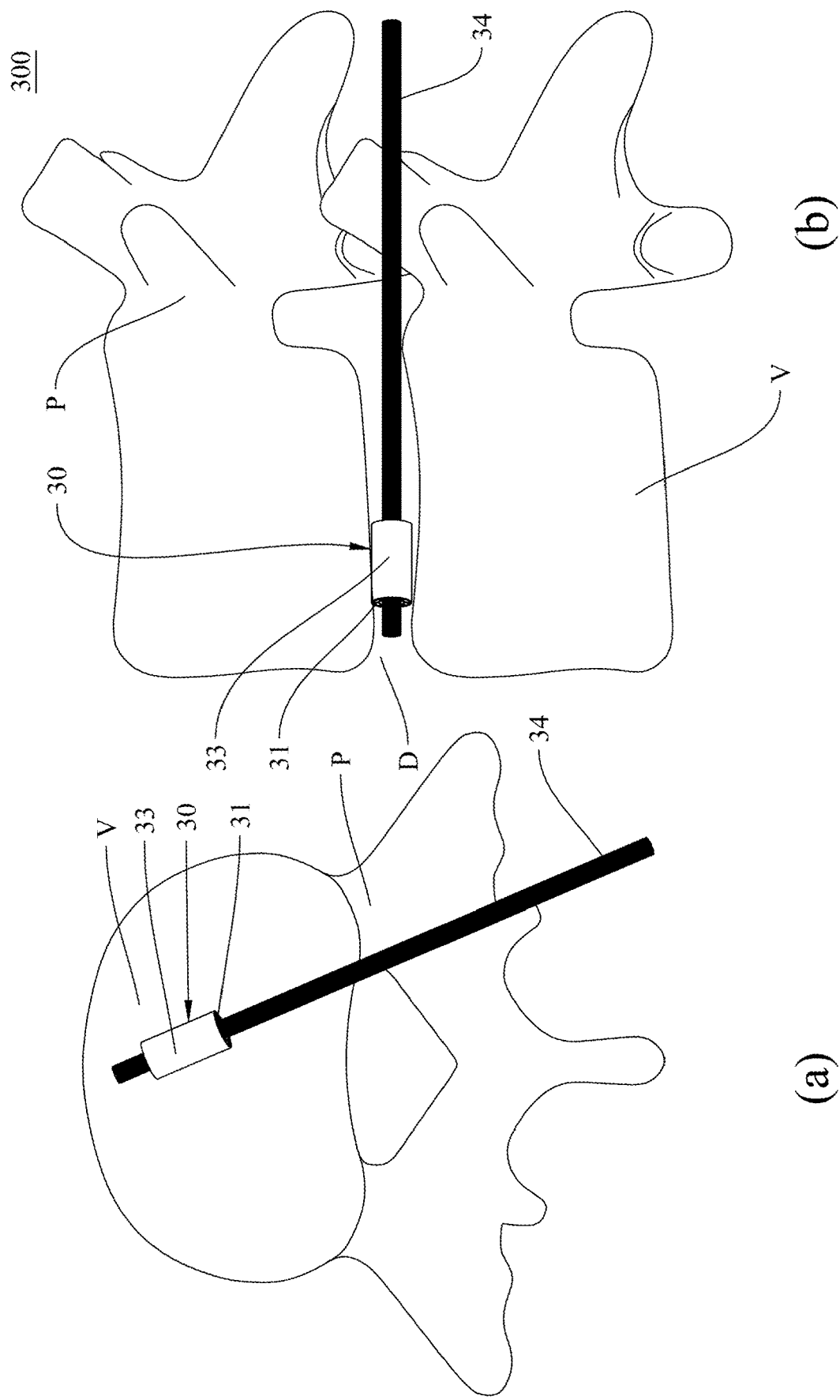
FIG. 14 includes an axial view (a) and a left side view (b) showing how the implant system in FIG. 13 is further operated (to position the support element)
Figure 15:
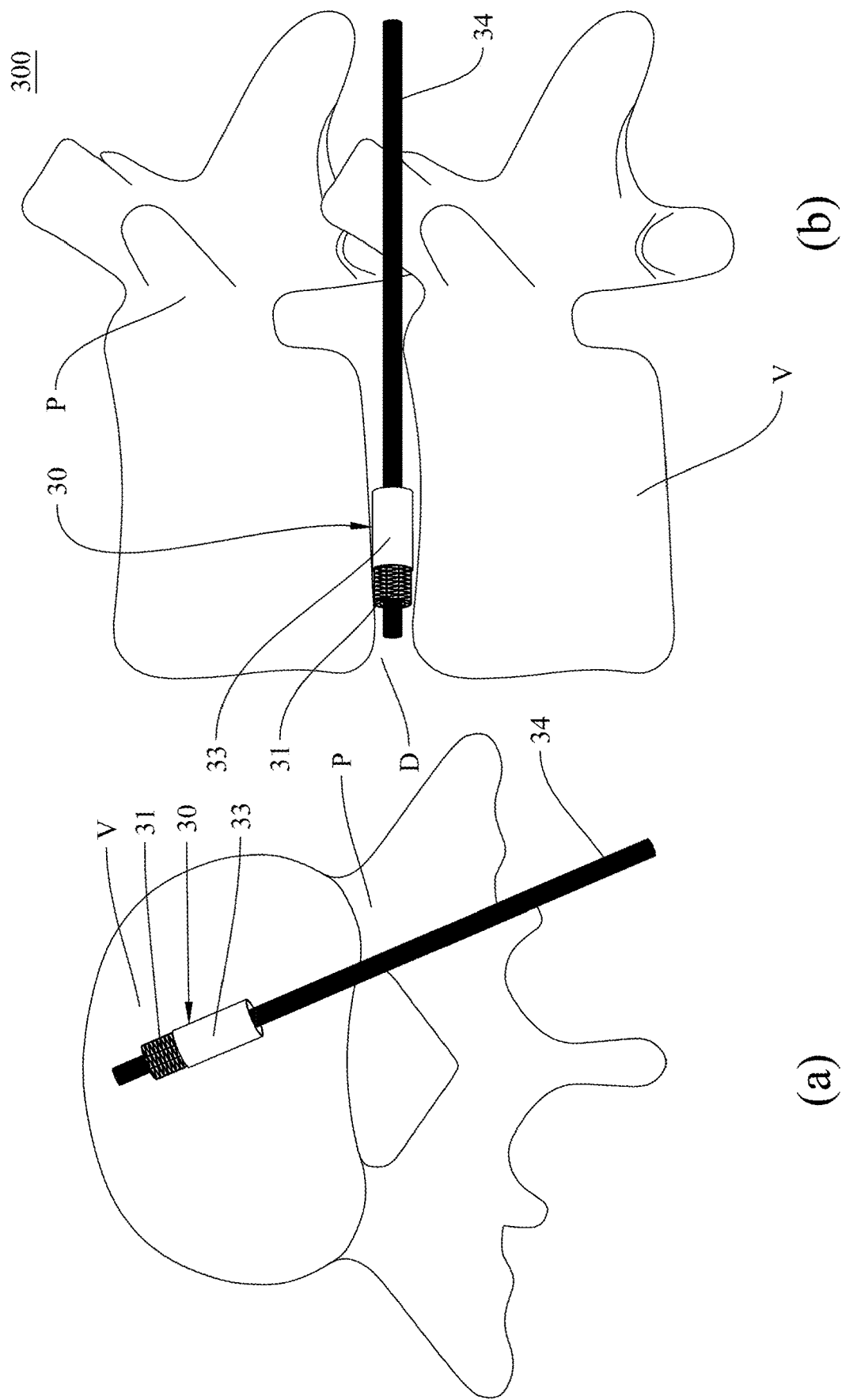
FIG. 15 includes an axial view (a) and a left side view (b) showing how the implant system in FIG. 14 is further operated (to remove the limiting member)

Once the guiding member 34 is in place, referring to FIG. 14, the contracted (i.e., non-expanded) support element 31, which is constrained within the limiting member 33, is guided into the intervertebral disc D along the guiding member 34 until the target position is reached, e.g., until the contracted support element 31 is properly positioned at the center of the intervertebral disc D. Next, referring to FIG. 15, the limiting member 33 is removed from the contracted support element 31.

Figure 16:
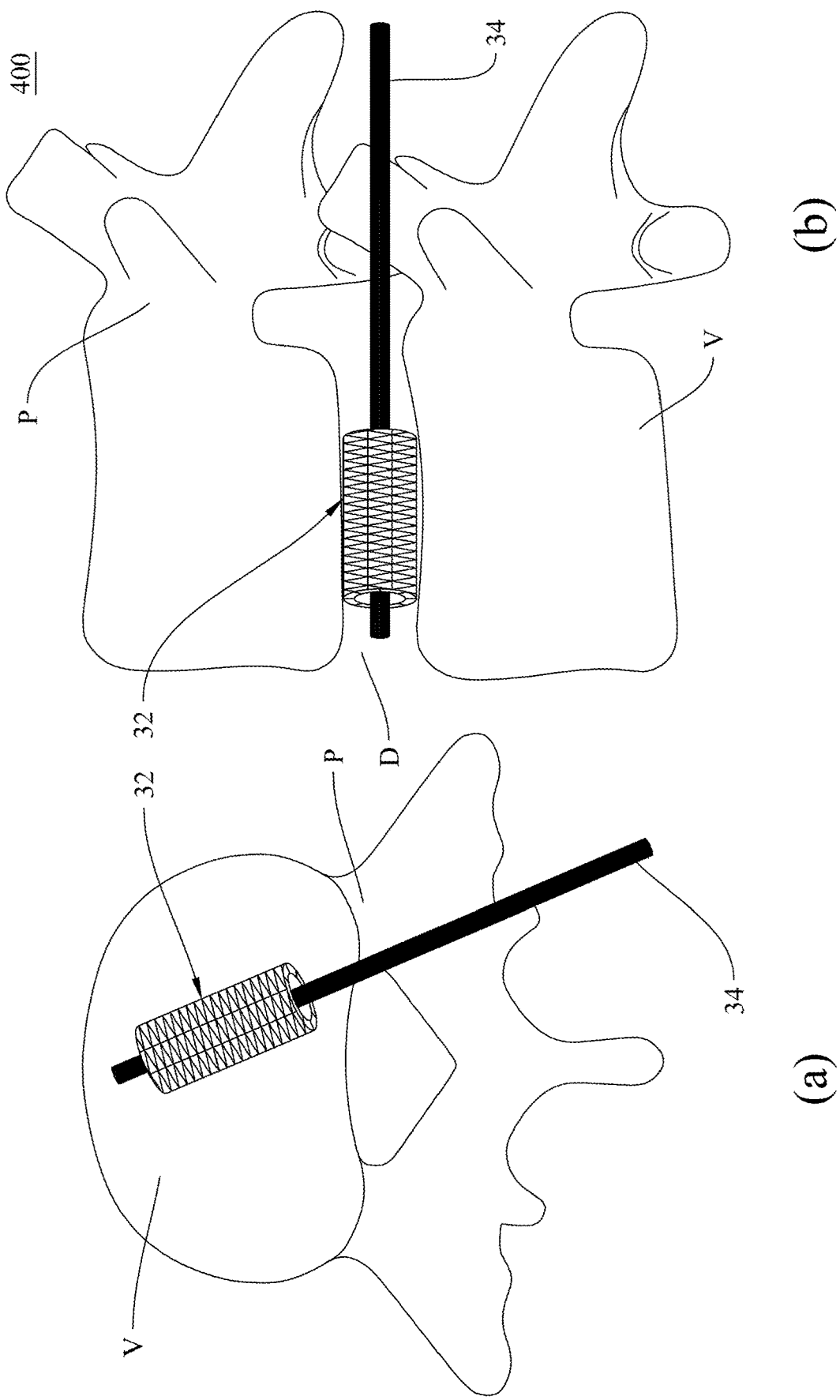
FIG. 16 includes an axial view (a) and a left side view (b) showing how the implant system in FIG. 15 is further operated (allowing the support element to expand into a distended configuration)

Finally, referring to FIG. 16, the contracted support element 31 expands elastically to the preset dimensions (i.e., turns into the distended support element 32) thanks to its shape memory and tightly contacts to the corresponding outer walls of the adjacent vertebrae (i.e., the twelfth thoracic vertebra T12 and the first lumbar vertebra L1 connected by the intervertebral disc D). The distended support element 32 provides support in the intervertebral disc D and thereby pushes the connected vertebrae apart by the desired distance. If necessary, a plurality of support elements can be implanted horizontally or vertically (not shown) to enlarge the areas by which to push apart the connected vertebrae. Thus, the support element of the present invention and the implant systems 300, 400 containing the same overcome such drawbacks of the conventional interosseous implantation operations as the necessity of complicated tools and the clinical expedient of using an inadequately sized support element (e.g., an intervertebral cage), which results in insufficient areas of contact between the implanted support element and the adjacent bones (e.g., vertebrae) and therefore either allows the implanted support element to sink into or slide away from the vertebrae or contributes little to intervertebral fusion such that a false joint is formed. In addition, the support element of the invention is structurally simple, compact in size, and hence applicable to the posterolateral approach and intervertebral foramen approach of intervertebral fusion without being subject to the entrance limitations imposed by the spinal cord and spinal nerves; thus, the invention enables the use of support elements that are adequately sized to provide sufficient support.

Figure 17:
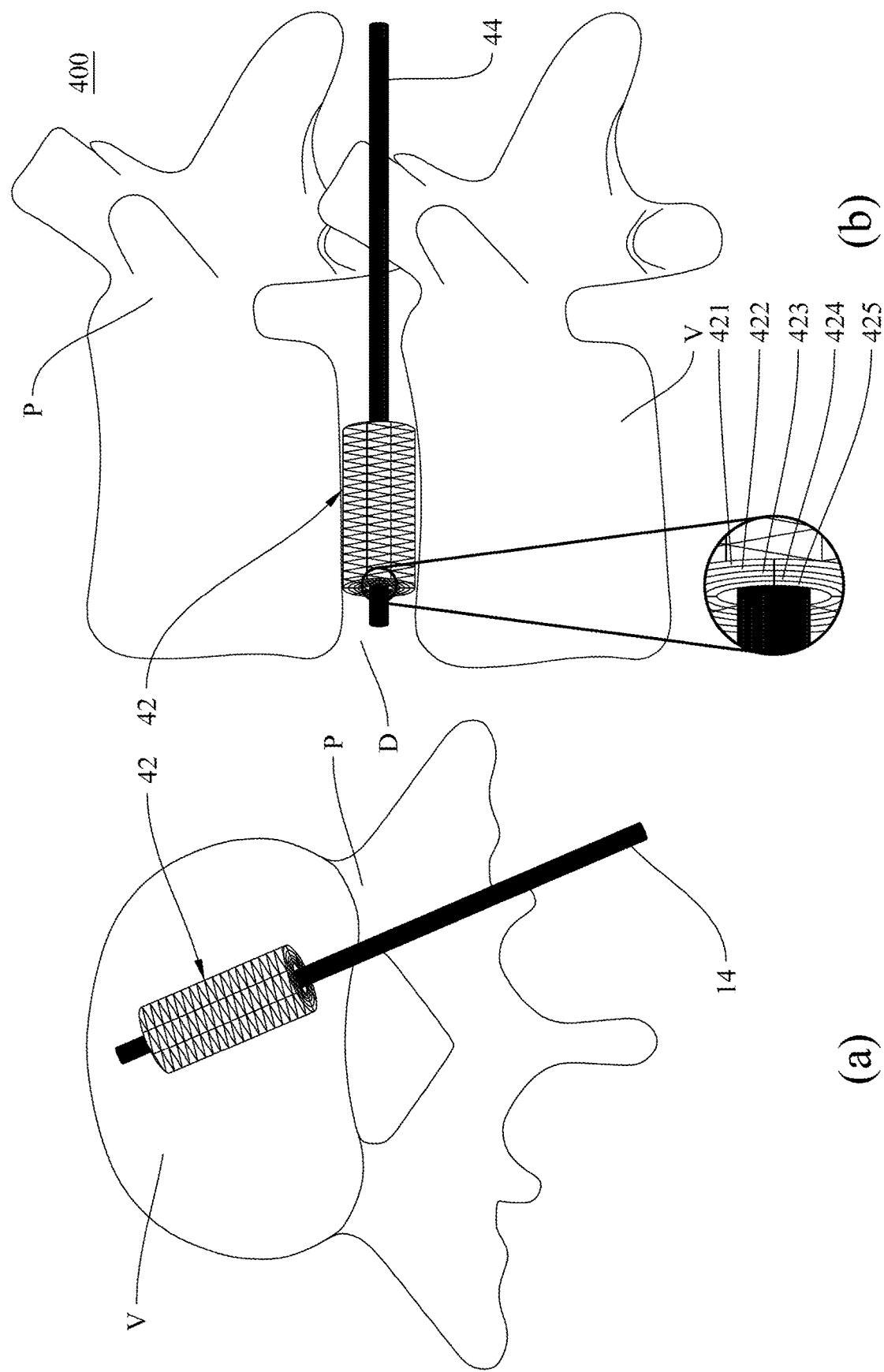
FIG. 17 includes an axial view (a) and a left side view (b) showing how the implant system according to still another preferred embodiment of the invention is operated (to have a plurality of support elements nested in one another).

The implant system 400 includes the foregoing support element as the first support element 421 and another foregoing support element (or a plurality of other foregoing support elements) in the distended hollow nestable structure of the first support element 421. The one or the plurality of other support elements are nested sequentially, in the distended configuration, in the hollow nestable structure of the first support element 421 as shown in FIG. 17. To nest a plurality of support elements 42 within one another, a support element is implanted into the intervertebral disc D with the guidance of the guiding member 44 in the same way as described above and then expands into the distended configuration to serve as the first support element 421, which contacts to the corresponding outer walls of the adjacent vertebrae, and a second support element 422, which is slightly smaller than the first support element 421, is implanted at the same site by the same method and, after elastic expansion, tightly contacts to the inner wall of the first support element 421 to provide more support or push the connected vertebrae further away from each other. If necessary, an appropriate number of support elements can be further implanted into the interosseous space. For example, a third support element 423, a fourth support element 424, and a fifth support element 425 are sequentially guided into and nested in the subject's intervertebral disc D to form the nested configuration shown in FIG. 17 and thereby achieve the desired supported height.

According to the above, a plurality of support elements of the present invention for implantation into or between a subject's bones can be sequentially implanted into a bone or between two connected bones to form a nested configuration. As a single contracted support element of the invention is small and easy to implant, a sufficient number of support elements can be implanted into or between a patient's bones according to practical needs. The implant system of the invention utilizes the elastic restoration ability of the support elements so that, once a small (i.e., contracted) support element is implanted and, after elastic expansion, tightly contacts to the inner wall of a bone or the corresponding outer walls of two connected bones, a second small (i.e., contracted) support element can be guided into the bone or the space between the connected bones along the same axis (i.e., the guiding member) before expanding elastically and contacting precisely to the inner wall of the first support element. By the same token, three or more support elements can be guided into and nested in a subject's bone or interosseous space in turn. The expanded support elements will not come off or leave the target location because they tightly contacts to the bone wall(s) either directly or indirectly. The invention is advantageous in that only a small incision (of the size of the contracted configuration of the support element of the invention) is required for implanting one or a plurality of support elements into a bone or between two connected bones to support the bone sufficiently or to expand the interosseous space to the desired extent.

As above, the present invention provides a support element that stays in a contracted configuration, and hence remains relatively small, before implantation into a subject's bone or between two connected bones so as to facilitate the implantation, allowing a minimally invasive, small-incision surgical operation to be performed clinically. Once implanted into the subject's bone or between the connected bones, the support element of the present invention expands elastically into a distended configuration and contacts to the inner wall of the bone to be treated or the corresponding outer walls of the bones to be treated, thereby expanding the fractured/collapsed bone or providing support between the connected bones. This support element is an improvement over the one-size implants used in the conventional implantation techniques because an existing one-size implant cannot "be a single micro-unit before implantation into or between a subject's bones and turn into a larger yet complete block after the implantation". In addition, unlike the traditional one-size implants, the support element of the invention will not rupture the affected bone structure (e.g., a pedicle) or injure the surrounding nerves (e.g., the spinal cord or spinal nerves), blood vessels (e.g., the abdominal aorta or the vertebral arteries), or other important tissues (e.g., the ureters) during implantation; nor provide inadequate support due to an expediently less-than-required size. If necessary, a plurality of the support elements of the present invention can be nested inside one another in the distended configuration after implantation into a bone or between two connected bones, and the nesting process can continue until the support provided by the entire implant system reaches the desired level. Thus, in the limited, tiny space in a single collapsed bone or between two connected bones, a plurality of the support elements of the invention can be put together to effectively restore the single collapsed bone or provide support between the connected bones. The number of the support elements to be implanted depends on the height of the bone to be restored or the distance between the connected bones to be supported. Theoretically, a single bone or the space between two connected bones can be filled with as many support elements of the invention as needed. When a plurality of the support elements of the present invention are implanted, all the support elements expand elastically in the same direction, and each support element contacts tightly to either the inner wall of a bone, the corresponding outer walls of adjacent bones, or the inner wall of a previous support element and hence will not come loose. Furthermore, the support element of the present invention has a hollow nestable structure, which can be filled with an autologous, heterologous, or artificial bone graft as clinically needed to help increase the density of, grow, and thereby heal a fractured bone.

The present invention is more detailed illustrated by the above preferable example embodiments. While example embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. An implant system for implantation into or between a subject's bones, comprising:
   a first expanding support element; and
   one or a plurality of additional expanding support elements, in which the one or a plurality of additional expanding support elements thereof respectively define a second to n-th expanding support element;
   wherein the expanding support element is a hollow nestable structure having expandable elasticity, so as to change from a contracted configuration to preset dimensions of a distended configuration, and the expanding support element is configured for being elastically self-expandable into its distended configuration;
   wherein the second expanding support element being slightly smaller in diameter than the first expanding support element and configured to increase contact with an inner wall of the first expanding support element after elastic expansion; sequentially, the n-th expanding support element being slightly smaller in diameter than the (n−1)-th expanding support element and configured to increase contact with an inner wall of the (n−1)-th expanding support element after elastic expansion, so that the distended configurations of the n-th expanding support elements are sequentially nestable into the distended configurations of the (n−1)-th expanding support element; and the first expanding support element and the one or a plurality of additional expanding support elements therefore form a nested structure which being configured to directly provide sufficient expanding support and mechanical strength of the bones or to expand an interosseous space to the desired extent.

2. The implant system of claim 1, wherein one of the subject's bones is a vertebra.

3. The implant system of claim 1, wherein the expanding support element is a reticular structure.

4. The implant system of claim 1, wherein the expanding support element composed of a material comprising a metal or an elastomer.

5. The implant system of claim 4, wherein the material of the expanding support element comprises nickel-titanium alloys.

6. The implant system of claim 1, wherein the expanding support element is a hollow cylinder.

7. The implant system of claim 1, wherein the implant system further comprises a guiding member which is configured to pass through the hollow nestable structure of the expanding support element.

* * * * *